(12) United States Patent
Rahman

(10) Patent No.: US 12,207,827 B2
(45) Date of Patent: Jan. 28, 2025

(54) INSTRUMENTS, SYSTEMS, AND METHODS OF USING

(71) Applicant: Paragon 28, Inc., Englewood, CO (US)

(72) Inventor: Naser Rahman, Dover, DE (US)

(73) Assignee: Paragon 28, Inc., Englewood, CO (US)

( * ) Notice: Subject to any disclaimer, the term of this patent is extended or adjusted under 35 U.S.C. 154(b) by 250 days.

(21) Appl. No.: 17/663,563

(22) Filed: May 16, 2022

(65) Prior Publication Data

US 2022/0273320 A1 Sep. 1, 2022

Related U.S. Application Data

(63) Continuation of application No. PCT/US2020/070786, filed on Nov. 13, 2020.

(Continued)

(51) Int. Cl.
| | |
|---|---|
| A61B 17/16 | (2006.01) |
| A61B 17/72 | (2006.01) |
| A61B 17/88 | (2006.01) |
| A61F 2/42 | (2006.01) |
| A61F 2/46 | (2006.01) |
| A61B 17/00 | (2006.01) |
| A61B 17/92 | (2006.01) |

(52) U.S. Cl.
CPC ...... *A61B 17/1697* (2013.01); *A61B 17/7291* (2013.01); *A61B 17/8872* (2013.01); *A61F 2/4225* (2013.01); *A61F 2/4606* (2013.01); *A61B 2017/00477* (2013.01); *A61B 17/921* (2013.01)

(58) Field of Classification Search
CPC .............. A61B 17/921; A61B 17/7291; A61B 17/8872; A61F 2/4225; A61F 2/4606
See application file for complete search history.

(56) References Cited

U.S. PATENT DOCUMENTS

| | | | |
|---|---|---|---|
| 4,246,662 | A | 1/1981 | Pastrick |
| 5,207,712 | A | 5/1993 | Cohen |

(Continued)

FOREIGN PATENT DOCUMENTS

| | | |
|---|---|---|
| FR | 2720623 | 12/1995 |
| WO | 2011110784 | 9/2011 |

OTHER PUBLICATIONS

International Search Report and Written Opinion of the International Searching Authority for PCT/US2020/070786, Mar. 25, 2021, 14 pages.

(Continued)

*Primary Examiner* — Matthew J Lawson
(74) *Attorney, Agent, or Firm* — Heslin Rothenberg Farley & Mesiti P.C.; Jacquelyn A. Graff, Esq.

(57) ABSTRACT

An implant insertion and removal system, including an insertion instrument that has a body portion with a handle portion at a first end of the body portion and a coupling member extending away from the handle portion to a second end of the body portion, and an engagement member rotatably coupled to the coupling member of the body portion. Specifically, instruments and systems used for hammertoe procedures for correcting bone deformities in the lower extremity. A surgical method including preparing a joint and inserting an implant into the proximal and middle phalanx using an insertion instrument.

19 Claims, 12 Drawing Sheets

Related U.S. Application Data

(60) Provisional application No. 62/936,164, filed on Nov. 15, 2019.

(56) References Cited

U.S. PATENT DOCUMENTS

| | | |
|---|---|---|
| 5,480,447 A | 1/1996 | Skiba |
| 5,593,409 A | 1/1997 | Michelson |
| 5,827,286 A | 10/1998 | Incavo |
| 5,902,304 A | 5/1999 | Walker |
| 6,008,431 A | 12/1999 | Caldarise |
| 6,123,705 A | 9/2000 | Michelson |
| 6,726,722 B2 | 4/2004 | Walkenhorst |
| 7,041,106 B1 | 5/2006 | Carver |
| 7,641,675 B2 | 1/2010 | Lindemann |
| 8,021,367 B2 | 9/2011 | Bourke |
| 8,100,983 B2 | 1/2012 | Schulte |
| 8,414,583 B2 | 4/2013 | Prandi |
| 8,529,611 B2 | 9/2013 | Champagne |
| 8,597,337 B2 | 12/2013 | Champagne |
| 8,672,986 B2 | 3/2014 | Klaue |
| 8,685,024 B2 | 4/2014 | Roman |
| 8,715,325 B2 | 5/2014 | Weiner |
| 8,715,326 B2 | 5/2014 | Champagne |
| 8,834,572 B2 | 9/2014 | Averous |
| 8,864,804 B2 | 10/2014 | Champagne |
| 8,888,778 B2 | 11/2014 | Roman |
| 9,044,287 B2 | 6/2015 | Reed |
| 9,072,562 B2 | 7/2015 | Weiner |
| 9,072,564 B2 | 7/2015 | Reed |
| 9,168,074 B2 | 10/2015 | Prandi |
| 10,058,431 B2 | 8/2018 | Tyber |
| 11,998,453 B2 * | 6/2024 | Ek ............... A61F 2/30 |
| 2002/0169066 A1 | 11/2002 | Cassidy |
| 2003/0083689 A1 | 5/2003 | Simonson |
| 2004/0106997 A1 | 6/2004 | Lieberson |
| 2005/0240197 A1 | 10/2005 | Kmiec |
| 2006/0004376 A1 | 1/2006 | Shipp |
| 2006/0206044 A1 | 9/2006 | Simon |
| 2007/0093841 A1 | 4/2007 | Hoogland |
| 2007/0156241 A1 | 7/2007 | Reiley |
| 2007/0270711 A1 | 11/2007 | Gil |
| 2008/0065215 A1 | 3/2008 | Reiley |
| 2008/0147125 A1 | 6/2008 | Colleran |
| 2009/0012529 A1 | 1/2009 | Blain |
| 2009/0030422 A1 | 1/2009 | Parsons |
| 2010/0121329 A1 | 5/2010 | Ryan |
| 2010/0145386 A1 | 6/2010 | Greenhalgh |
| 2010/0168798 A1 | 7/2010 | Clineff |
| 2010/0198221 A1 | 8/2010 | Hearn |
| 2010/0211119 A1 | 8/2010 | Refai |
| 2010/0249934 A1 | 9/2010 | Melkent |
| 2010/0266979 A1 | 10/2010 | Karmon |
| 2011/0054545 A1 | 3/2011 | Champagne |
| 2012/0065692 A1 * | 3/2012 | Champagne ....... A61B 17/7291 606/301 |
| 2012/0221049 A1 | 8/2012 | Blain |
| 2012/0323243 A1 | 12/2012 | Moon |
| 2013/0030475 A1 | 1/2013 | Weiner et al. |
| 2013/0060295 A1 | 3/2013 | Reed et al. |
| 2013/0066383 A1 | 3/2013 | Anderson |
| 2013/0123862 A1 | 5/2013 | Anderson |
| 2013/0131822 A1 | 5/2013 | Lewis et al. |
| 2013/0150965 A1 | 6/2013 | Taylor |
| 2013/0165982 A1 | 6/2013 | Ek et al. |
| 2013/0190831 A1 | 7/2013 | Ek et al. |
| 2013/0274814 A1 * | 10/2013 | Weiner ............... A61B 17/7291 606/301 |
| 2013/0317559 A1 | 11/2013 | Leavitt |
| 2013/0325077 A1 | 12/2013 | Champagne et al. |
| 2013/0338785 A1 | 12/2013 | Wong |
| 2014/0052196 A1 | 2/2014 | McGinley et al. |
| 2014/0107712 A1 | 4/2014 | Fallin et al. |
| 2014/0142715 A1 | 5/2014 | McCormick |
| 2014/0188239 A1 | 7/2014 | Cummings |
| 2014/0222091 A1 | 8/2014 | Champagne et al. |
| 2014/0276825 A1 | 9/2014 | Brown et al. |
| 2014/0276827 A1 | 9/2014 | Roman et al. |
| 2014/0277183 A1 | 9/2014 | Stalcup et al. |
| 2014/0277186 A1 | 9/2014 | Granberry et al. |
| 2014/0277191 A1 | 9/2014 | Evans et al. |
| 2014/0277554 A1 | 9/2014 | Roman et al. |
| 2014/0309747 A1 | 10/2014 | Taylor et al. |
| 2015/0032108 A1 | 1/2015 | Roman |
| 2015/0073413 A1 | 3/2015 | Palmer et al. |
| 2015/0094778 A1 | 4/2015 | McCormick et al. |
| 2015/0112341 A1 | 4/2015 | Penzimer et al. |
| 2015/0112342 A1 * | 4/2015 | Penzimer ........... A61B 17/7291 606/63 |
| 2015/0142066 A1 * | 5/2015 | Shemwell .......... A61B 17/8888 606/301 |
| 2015/0150607 A1 | 6/2015 | Chen et al. |
| 2015/0164563 A1 | 6/2015 | Lewis |
| 2015/0190147 A1 | 7/2015 | Ferragamo et al. |
| 2015/0305789 A1 | 10/2015 | Weiner et al. |
| 2015/0374503 A1 | 12/2015 | Lovick et al. |
| 2016/0015437 A1 | 1/2016 | Elleby |
| 2016/0030095 A1 | 2/2016 | Roman et al. |
| 2016/0045324 A1 | 2/2016 | Austin et al. |
| 2016/0287407 A1 | 10/2016 | Patrick et al. |
| 2017/0000618 A1 | 1/2017 | Tyber et al. |
| 2017/0239059 A1 * | 8/2017 | Boublil ............... A61F 2/30771 |
| 2018/0021145 A1 | 1/2018 | Seavey et al. |
| 2018/0132920 A1 * | 5/2018 | Vikinsky ............ A61B 17/888 |
| 2018/0243018 A1 * | 8/2018 | Lintula .............. A61B 17/8897 |
| 2018/0256219 A1 * | 9/2018 | Lintula .............. A61B 17/8872 |
| 2018/0303615 A1 * | 10/2018 | Papaloïzos .......... A61F 2/30771 |

OTHER PUBLICATIONS

Ribeiro, C.H. et al., "A new fixation material for open-wedge tibial osteotomy for genu varum," The Knee, 2009, Issue 5, pp. 366-370.

* cited by examiner

INSTRUMENTS, SYSTEMS, AND METHODS OF USING

CROSS-REFERENCE TO RELATED APPLICATION

This application is a continuation of PCT Application No. PCT/US2020/070786 filed Nov. 13, 2020, and entitled "Instruments, Systems, and Methods of Using," which claims priority benefit under 35 U.S.C. § 119(e) of U.S. provisional application No. 62/936,164, filed Nov. 15, 2019, and entitled "Instruments, Systems, and Methods of Using," the disclosure of which are incorporated herein by reference in their entireties.

FIELD OF THE INVENTION

The present invention relates generally to general surgery, podiatric, and orthopaedic instruments used for inserting implants to correct bone deformities. More specifically, but not exclusively, the present invention relates to instruments, systems and methods for using the instruments and systems to correct bone deformities.

BACKGROUND OF THE INVENTION

Many disorders can affect toe or finger joints, causing pain and preventing the foot or hand from functioning as they should. These problems may be inherited from abnormally long toes, flat feet or high arches, or acquired from wearing poor fitting footwear or a fractured toe, which can further aggravate the deformities and cause more pain. Toe deformities in, for example, adults result mainly from an imbalance of the tendons, causing them to stretch or tighten abnormally. Arthritis is another major cause of discomfort and deformity in fingers and toes. The most common digital deformities in the foot are hammertoes, claw toes and overlapping and underlapping toes.

Podiatrists and orthopedists commonly use surgical procedures to alleviate the discomfort of, for example, a hammertoe and other abnormalities of the toe and finger joints and to prevent recurrence of the deformity. In the case of a hammertoe, surgeons may perform a proximal interphalangeal joint ("PIPJ") arthrodesis with the use of, for example, a Kirschner wire ("K-wire"), or insert a prosthetic device into adjoining phalanges of the toe, which serve to function as a normal knuckle or joint would. Currently available insertion instruments may be difficult to use or may lack stability.

Thus, new instruments are needed for improved insertion of implants to correct bone deformities.

SUMMARY OF THE INVENTION

Aspects of the present invention provide instruments and methods for correcting bone deformities in the foot.

In one aspect, provided herein is an implant insertion and removal system, including an insertion instrument. The insertion instrument including a body portion with a handle portion at a first end of the body portion and a coupling member extending away from the handle portion to a second end of the body portion. The implant insertion and removal system may also include an engagement member rotatably coupled to the coupling member. The implant insertion and removal system may also include an implant for coupling to the insertion instrument.

In another aspect, provided herein is an insertion instrument. The insertion instrument including a body portion with a handle portion at a first end of the body portion and a coupling member extending away from the handle portion to a second end of the body portion. The insertion instrument may also include an engagement member rotatably coupled to the coupling member.

In yet another aspect, provided herein is a surgical method. The surgical method includes, exposing a patient's joint and inserting a first k-wire into a base of the middle phalanx proximally. The method also includes retrograding the first k-wire from a tip of a toe, across a distal phalanx and a middle phalanx and inserting the first k-wire into a proximal phalanx. The method further includes pulling the first k-wire to position a tip of the first k-wire in the joint and inserting a second k-wire into the proximal phalanx. In addition, the method includes driving a drill across the second k-wire and into the proximal phalanx and removing the second k-wire from the patient's joint. Finally, the method may include driving the drill and the first k-wire into the middle phalanx and inserting an implant into the proximal phalanx and the middle phalanx using the insertion instrument.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
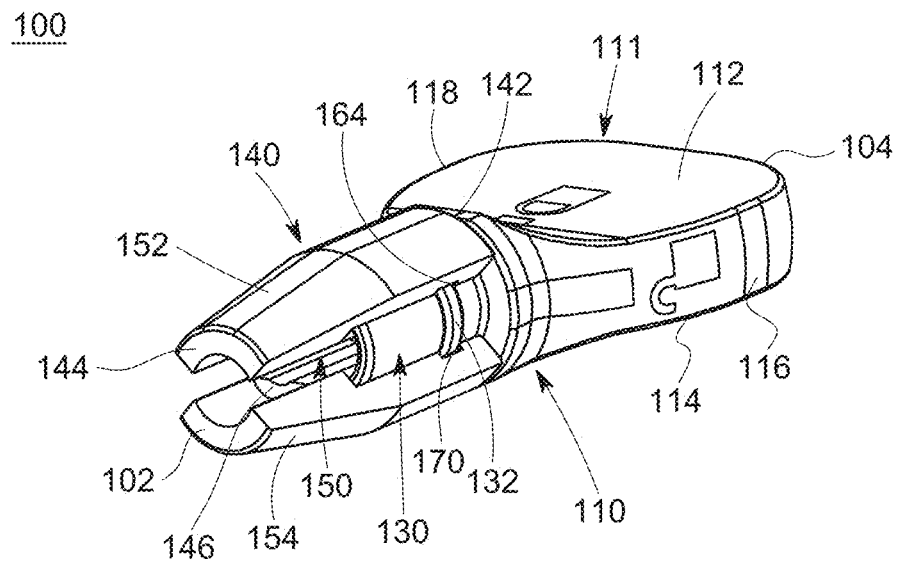
FIG. 1 is a first perspective view of an insertion instrument, in accordance with an aspect of the present disclosure.
Figure 2:
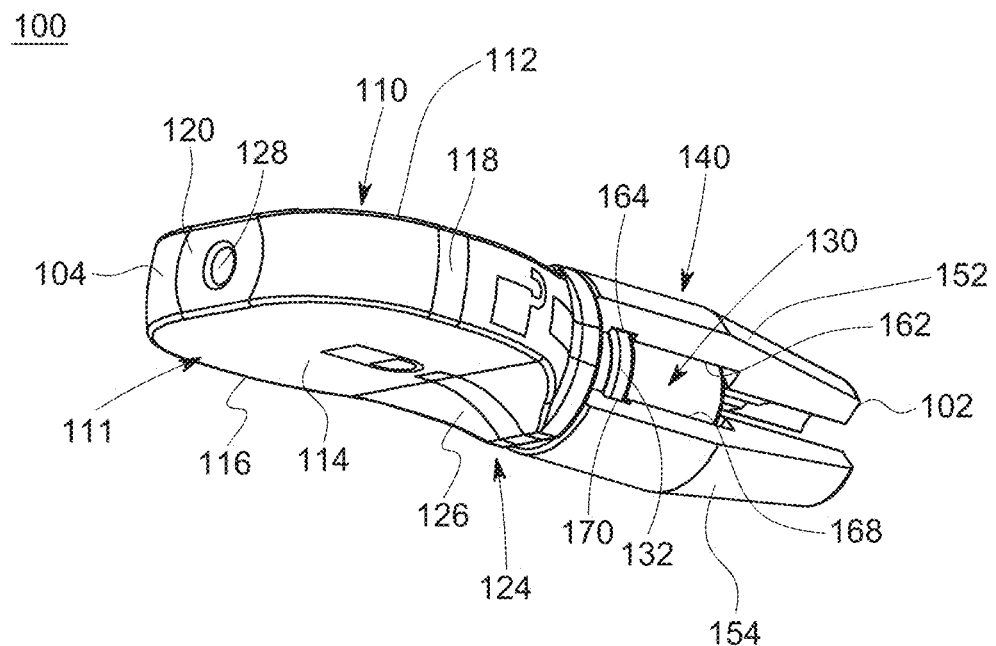
FIG. 2 is a second perspective view of the insertion instrument of FIG. 1, in accordance with an aspect of the present disclosure.
Figure 3:
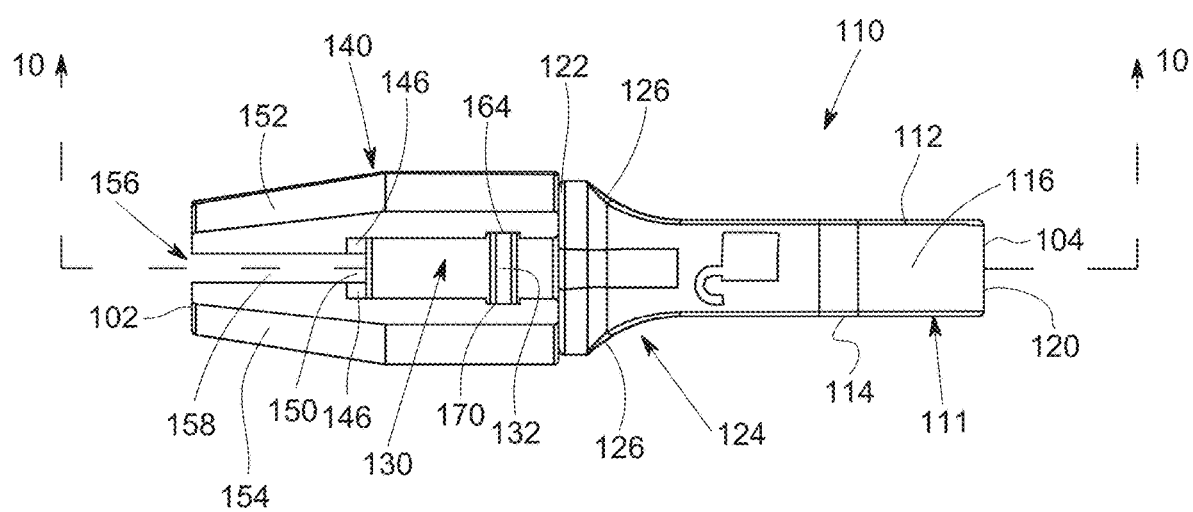
FIG. 3 is a first side view of the insertion instrument of FIG. 1, in accordance with an aspect of the present disclosure.
Figure 4:
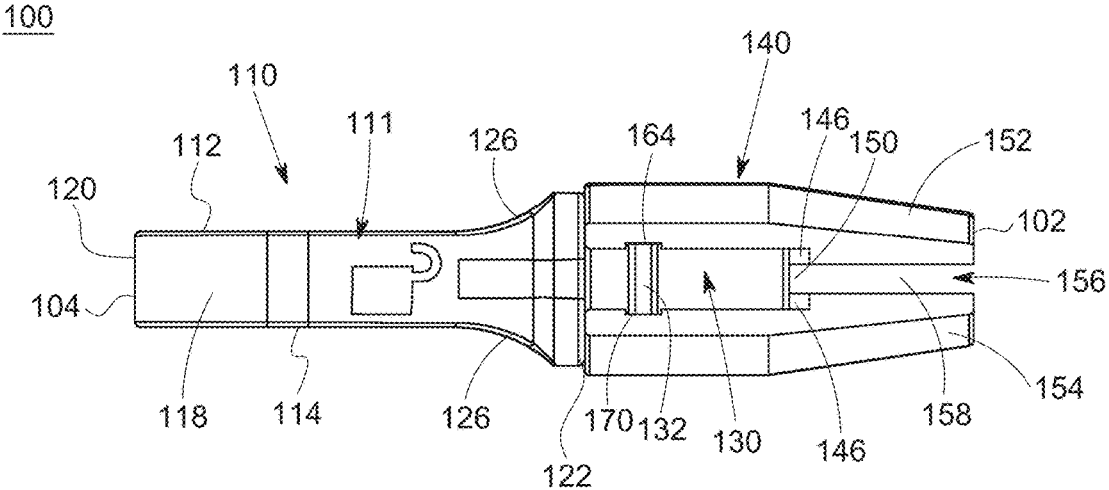
FIG. 4 is a second side view of the insertion instrument of FIG. 1, in accordance with an aspect of the present disclosure.
Figure 5:
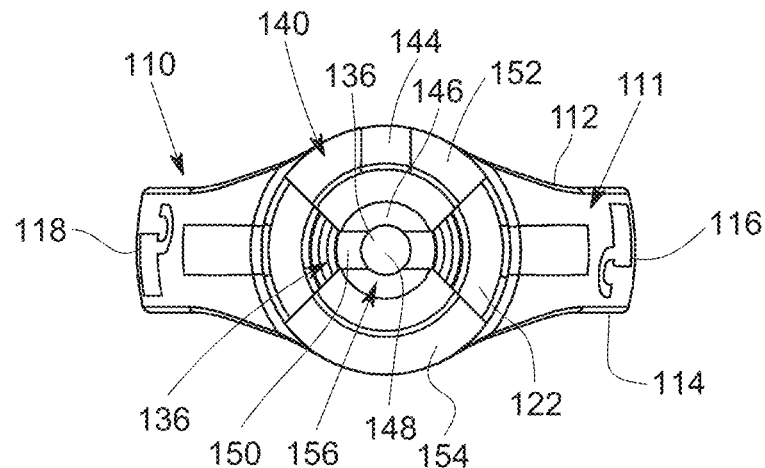
FIG. 5 is a first end view of the insertion instrument of FIG. 1, in accordance with an aspect of the present disclosure.
Figure 6:
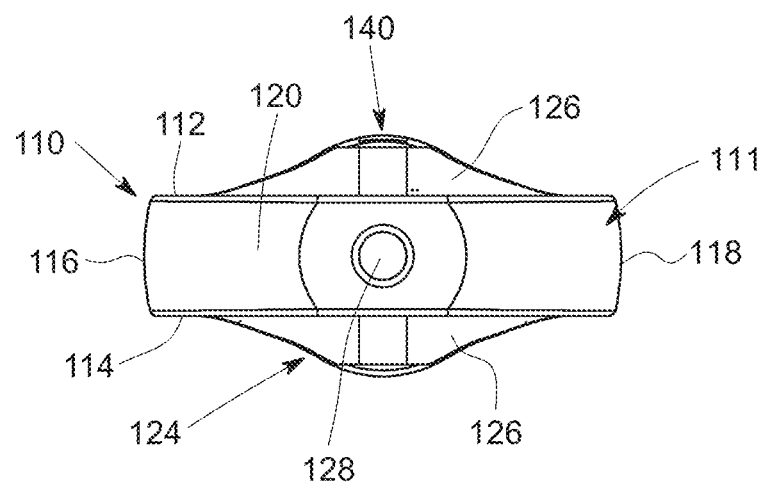
FIG. 6 is a second end view of the insertion instrument of FIG. 1, in accordance with an aspect of the present disclosure.
Figure 7:
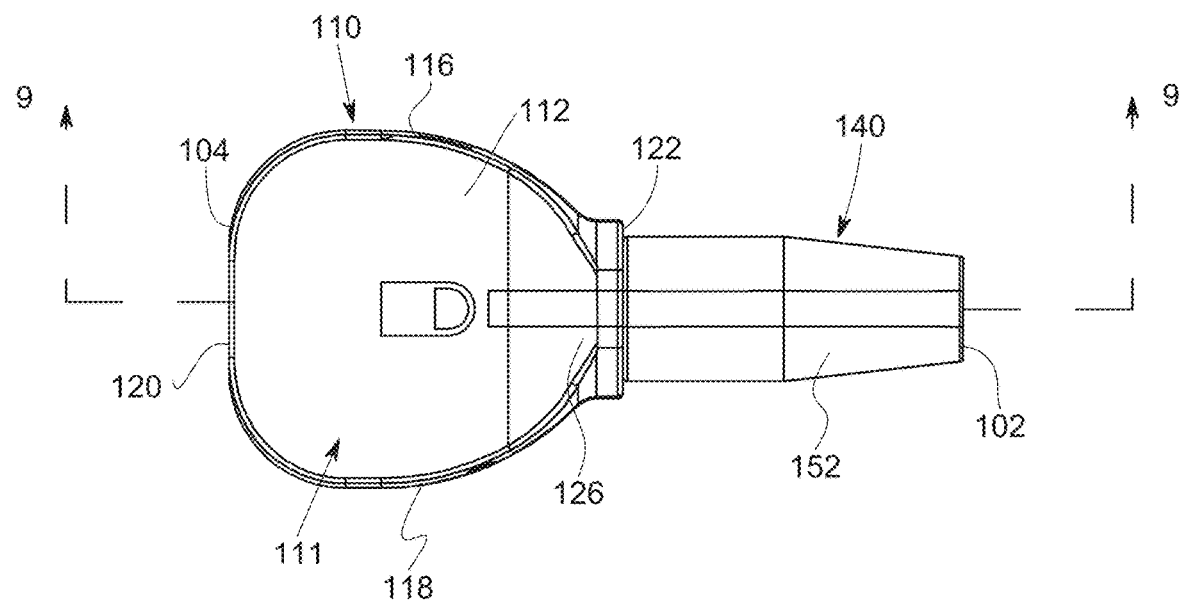
FIG. 7 is a top view of the insertion instrument of FIG. 1, in accordance with an aspect of the present disclosure.
Figure 8:
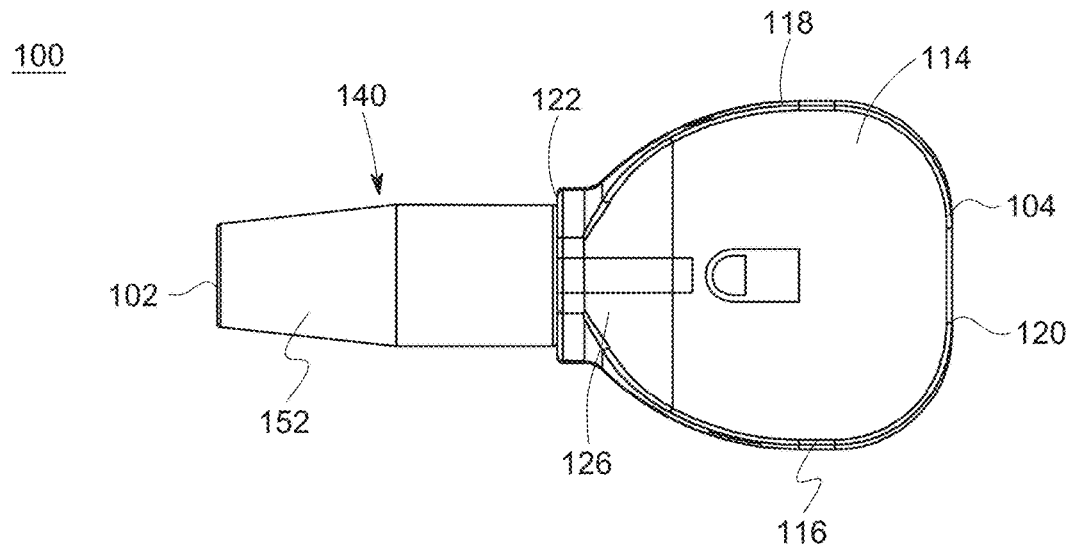
FIG. 8 is a bottom view of the insertion instrument of FIG. 1, in accordance with an aspect of the present disclosure.
Figure 9:
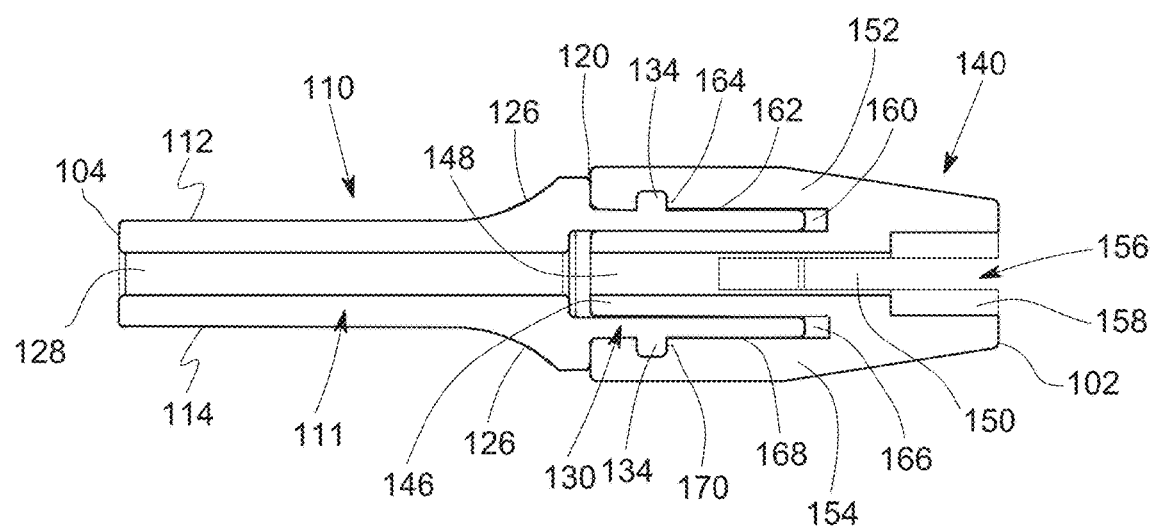
FIG. 9 is a cross-sectional view of the insertion instrument of FIG. 1 taken along line 9-9 in FIG. 7, in accordance with an aspect of the present disclosure.
Figure 10:
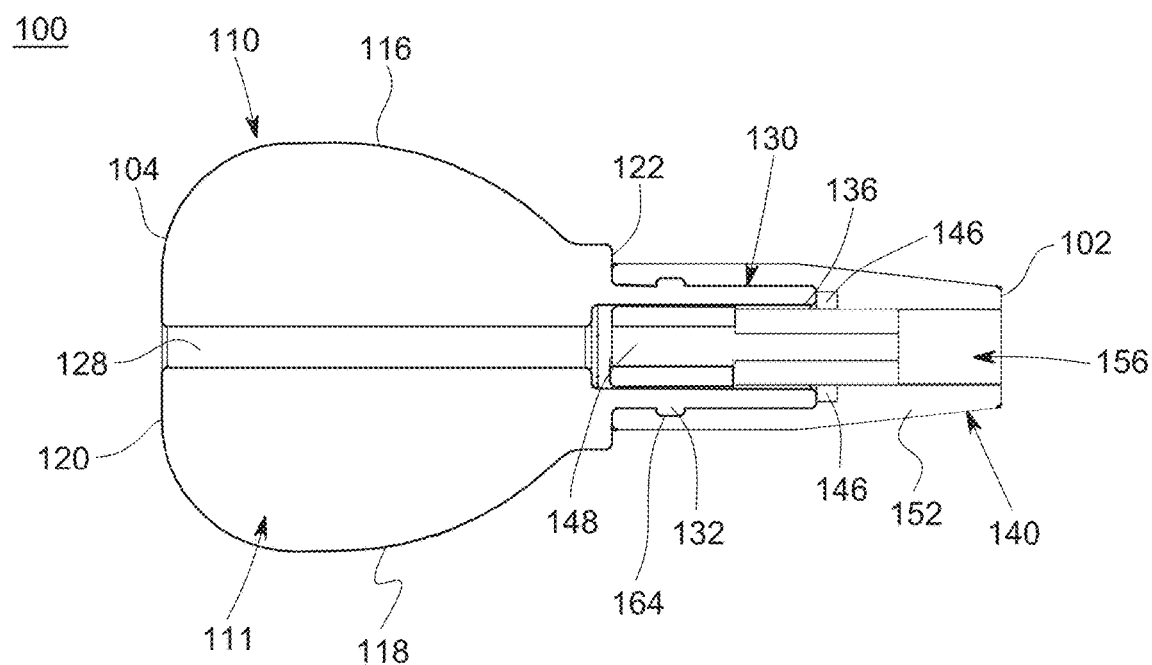
FIG. 10 is a cross-sectional view of the insertion instrument of FIG. 1 taken along line 10-10 in FIG. 3, in accordance with an aspect of the present disclosure.
Figure 11:
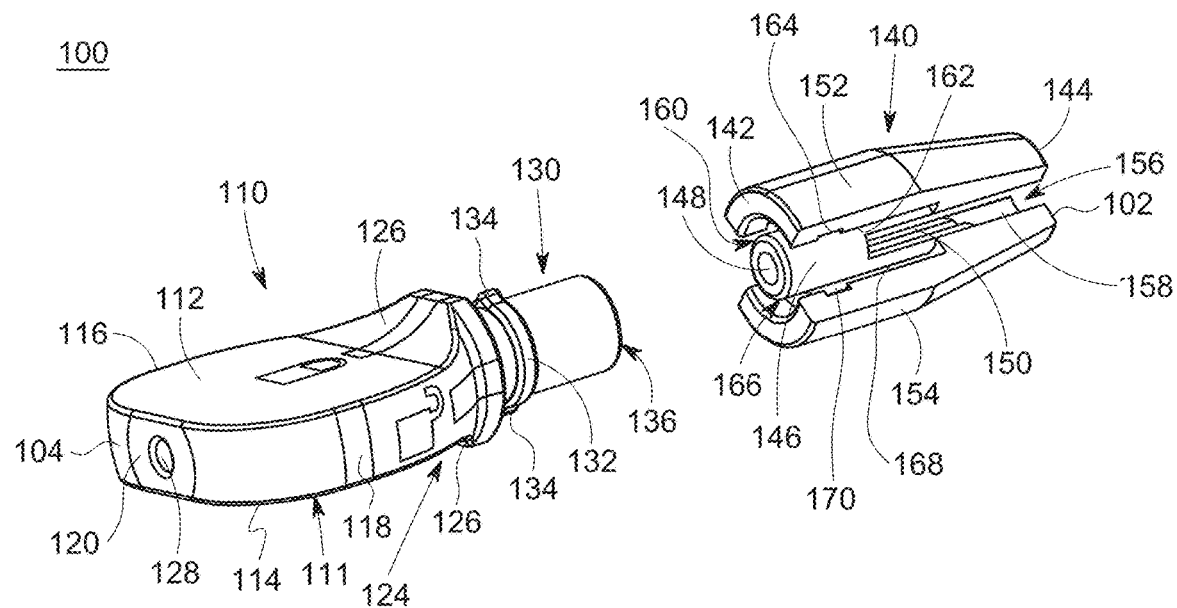
FIG. 11 is a first exploded, side perspective view of the insertion instrument of FIG. 1, in accordance with an aspect of the present disclosure.
Figure 12:
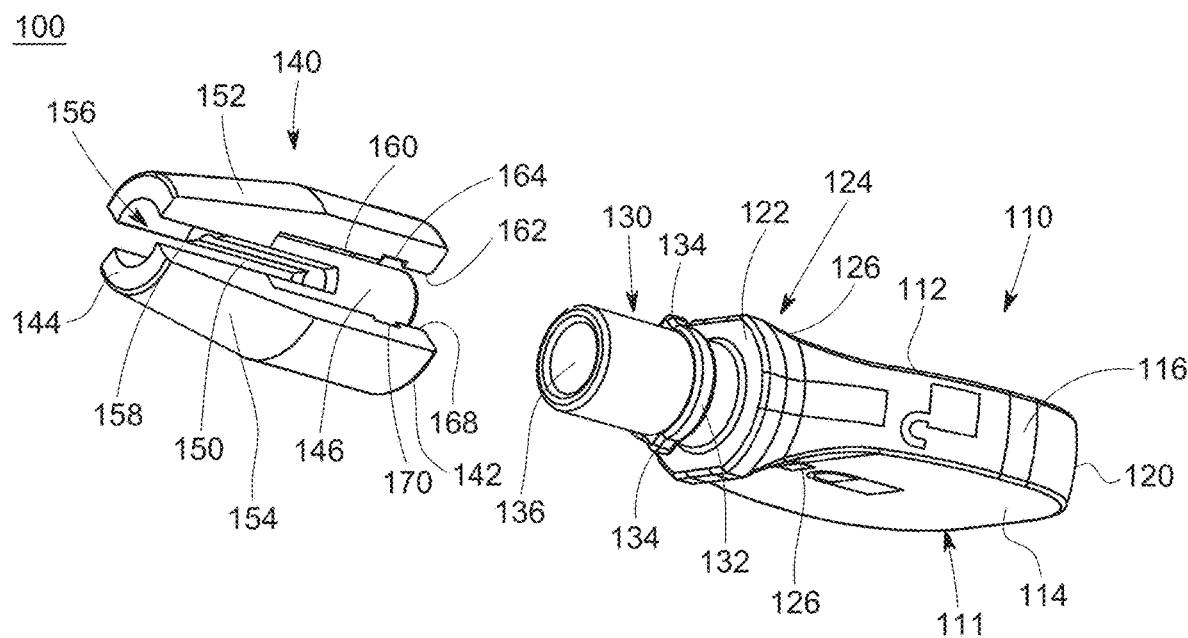
FIG. 12 is a second exploded, side perspective view of the insertion instrument of FIG. 1, in accordance with an aspect of the present disclosure.
Figure 13:
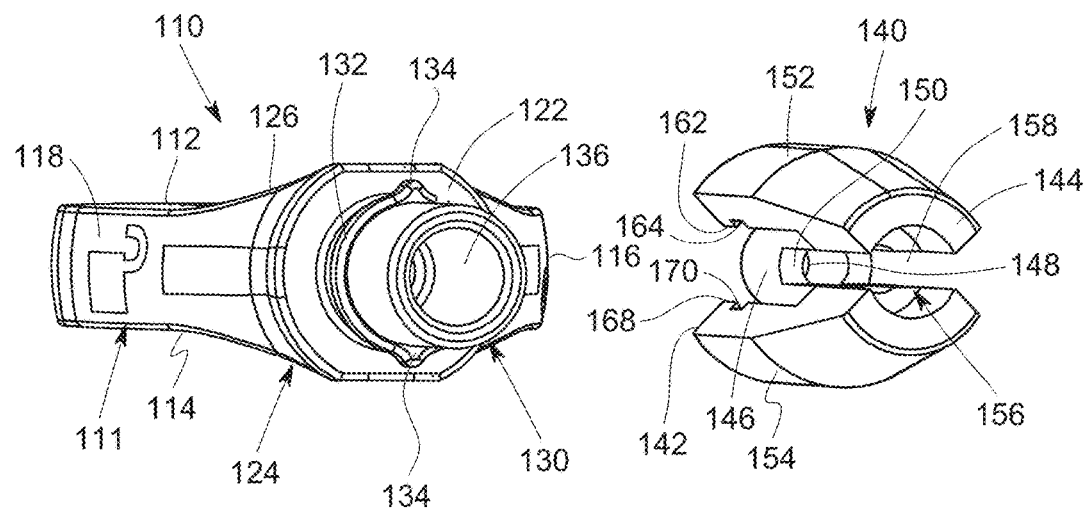
FIG. 13 is a first exploded, end perspective view of the insertion instrument of FIG. 1, in accordance with an aspect of the present disclosure.
Figure 14:
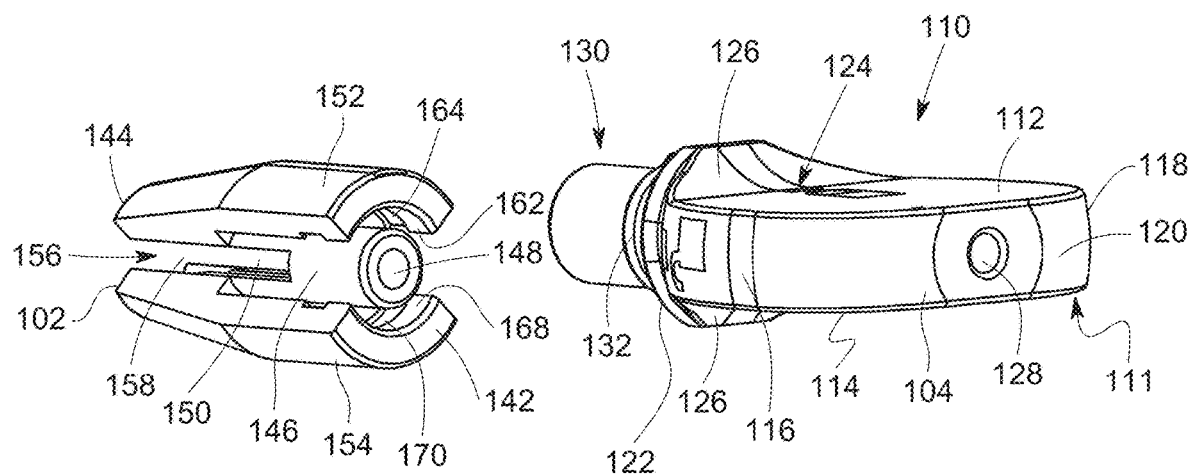
FIG. 14 is a second exploded, end perspective view of the insertion instrument of FIG. 1, in accordance with an aspect of the present disclosure.
Figure 15:
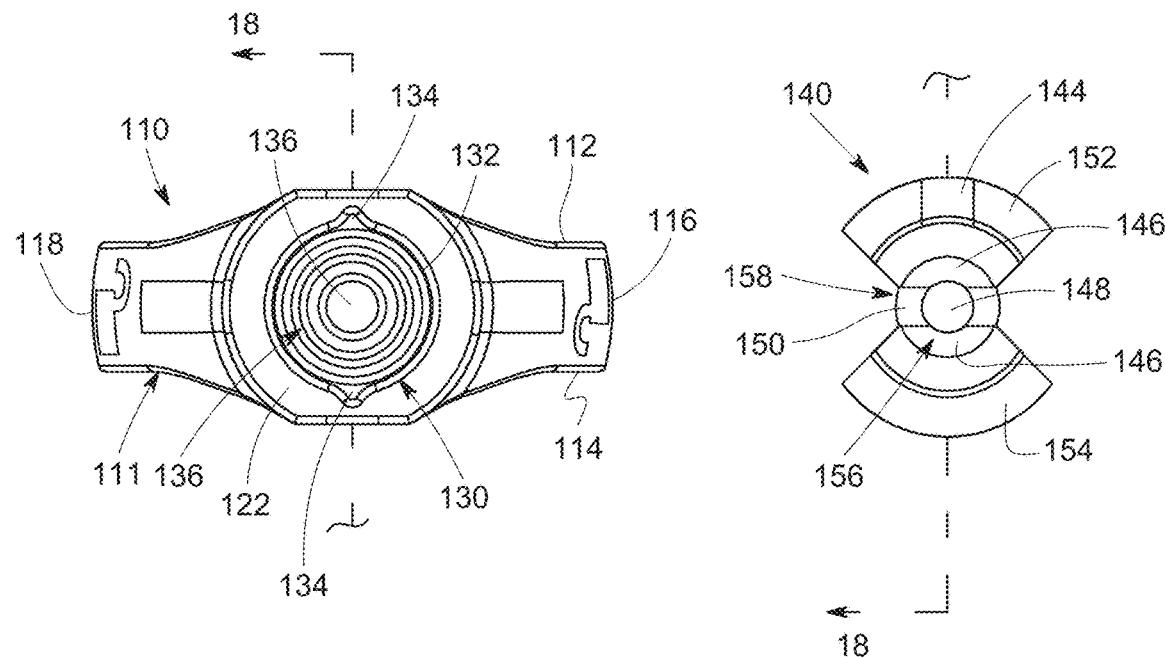
FIG. 15 is a first exploded end view of an insertion instrument of FIG. 1, in accordance with an aspect of the present disclosure.
Figure 16:
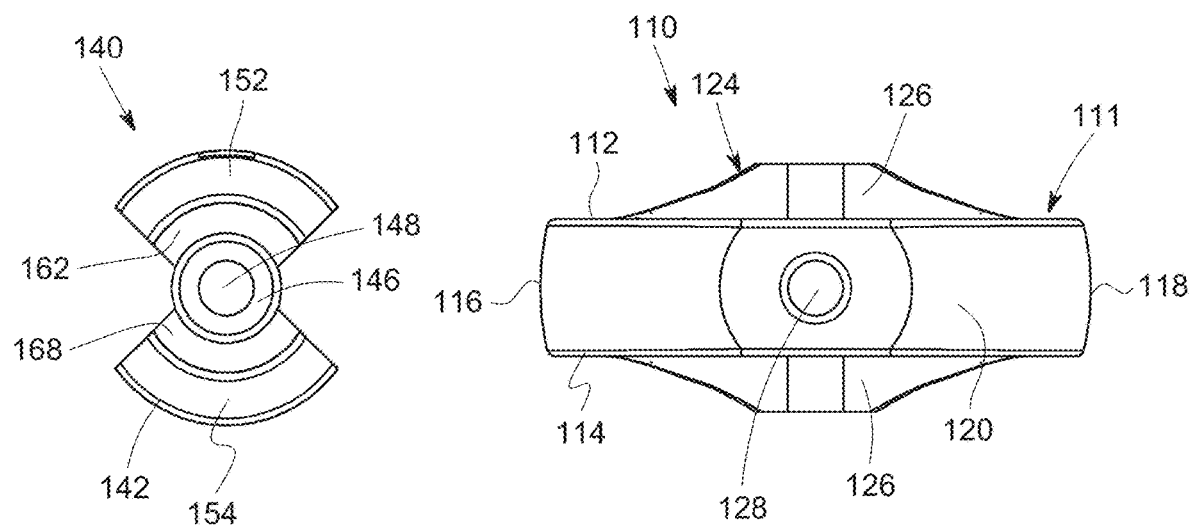
FIG. 16 is a second exploded end view of the insertion instrument of FIG. 1, in accordance with an aspect of the present disclosure.
Figure 17:
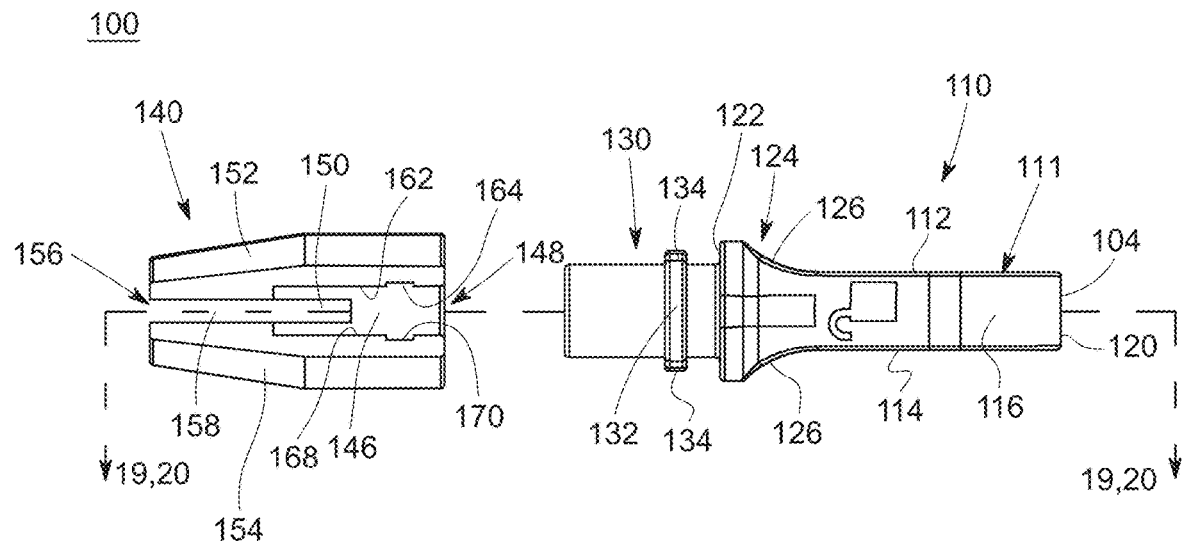
FIG. 17 is an exploded side view of the insertion instrument of FIG. 1, in accordance with an aspect of the present disclosure.

Generally stated, disclosed herein are instruments and systems for correcting bone deformities. Further, surgical methods for using the instruments and systems to correct bone deformities are discussed.

In this detailed description and the following claims, the words proximal, distal, anterior or plantar, posterior or dorsal, medial, lateral, superior and inferior are defined by their standard usage for indicating a particular part or portion of a bone or instrument according to the relative disposition of the natural bone or directional terms of reference. For example, "proximal" means the portion of a device or instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above, and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current instrumentation and methods are described herein with reference to use with the bones of the foot, ankle and lower leg may be used to describe the surfaces, positions, directions or orientations of the instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-26, there is illustrated one embodiment of an implant insertion and removal system including a an insertion instrument 100 and at least one implant 680, as shown in FIGS. 21-26. As shown in FIGS. 1-26, the insertion instrument 100 includes a body or handle portion 110 and an engagement member 140. The engagement member 140 may extend from the first end 102 of the insertion instrument 100 toward a second end 104 of the insertion instrument 100. The body portion 110 may extend from the second end 104 of the insertion instrument 100 toward the first end 102 of the insertion instrument 100. The engagement member 140 may be removably coupled to a second end of the body portion 110.

As shown in FIGS. 11-20, the body portion 110 may include a handle portion 111 and a coupling member 130 extending away from a second end of the handle portion 111.

The handle portion 111 may include a top surface 112 opposite a bottom surface 114, a first side portion 116 opposite a second side portion 118, and a first end portion 120 opposite a second end portion 122. The top surface 112 and bottom surface 114 may be, for example, planar and extend from the second end 104 of the instrument 100 to a neck portion 124. In an alternative embodiment, the top surface 112 and the bottom surface 114 may be, for example, curved or textured to provide alternative gripping surfaces for the user. The neck portion 124 may include, for example, tapered or curved surfaces 126 as the top surface 112 and bottom surface 114 extend from the planar portion to the second end portion 122. The second end portion 122 may have, for example, a first height extending between the top surface 112 and the bottom surface 114. In addition, the handle portion 111 may have, for example, a second height between the top surface 112 and the bottom surface 114. The first height may be, for example, larger than the second height. While the second end portion 122 may also have, for example, a first width extending between the first side portion 116 and the second side portion 118. In addition, the handle portion 111 may have, for example, a second width between the first side portion 116 and the second side portion 118. The first width may be, for example, larger than the second width. The handle portion 111 may also include a first opening segment 128 extending into the handle portion 111 from a second end 104 of the instrument 100 toward the coupling member 130.

Figure 18:
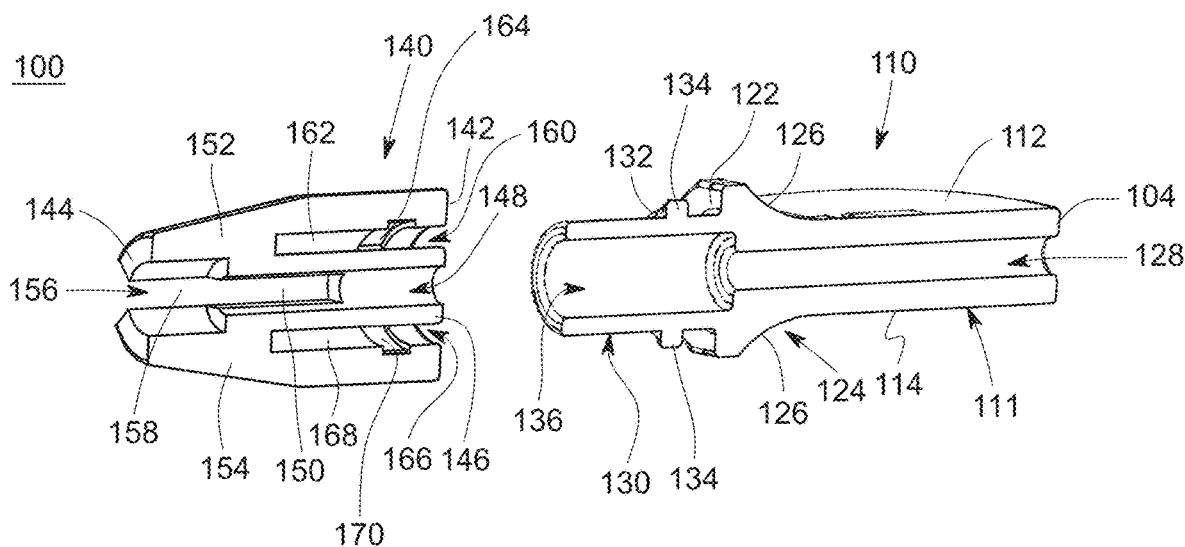
FIG. 18 is an exploded cross-sectional, perspective view of the insertion instrument FIG. 1 taken along line 18-18 in FIG. 15, in accordance with an aspect of the present disclosure.
Figure 19:
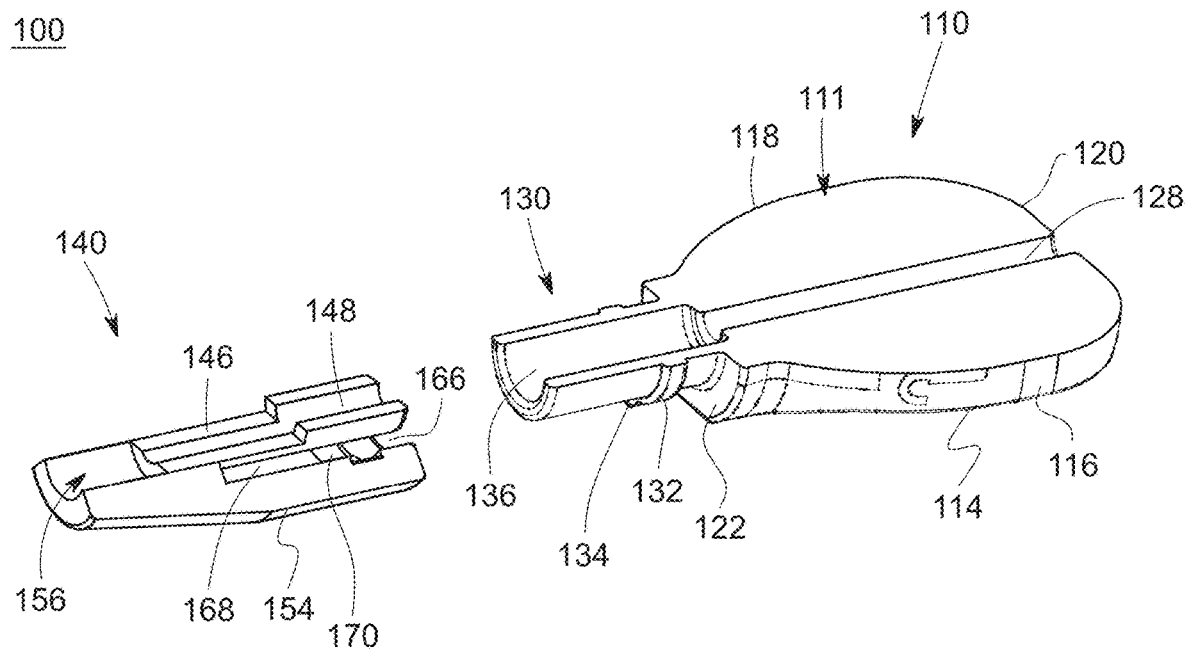
FIG. 19 is an exploded cross-sectional, perspective view of the insertion instrument of FIG. 1 taken along line 19-19 in FIG. 17, in accordance with an aspect of the present disclosure.
Figure 20:
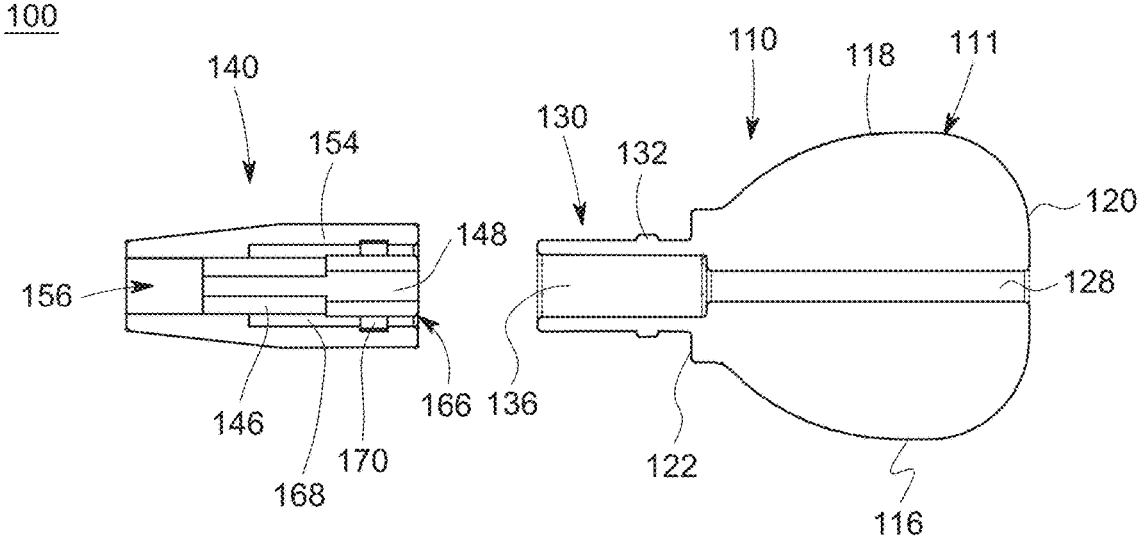
FIG. 20 is an exploded cross-sectional, top view of the insertion instrument of FIG. 1 taken along line 20-20 in FIG. 17, in accordance with an aspect of the present disclosure.

With continued reference to FIGS. 11-20, the coupling member 130 may include a protrusion or circumferential protrusion 132 extending out from the coupling member 130. The protrusion 132 may be, for example, positioned circumferentially around the coupling member 130 between the second end portion 122 and a first end 102 of the instrument 100. The protrusion 132 may further include at least one tooth, engagement tooth or locking tooth extending away from the protrusion 132. In the depicted embodiment, the protrusion 132 includes two locking teeth 134 positioned opposite each other. The coupling member 130 may further include a second opening segment 136 extending into the instrument 100 from the first end 102 of the instrument 100. The second opening segment 136 may extend from the first end 102 of the instrument 100 until it engages the first opening segment 128. As shown in FIGS. 18-20, the first opening segment 128 has a first diameter and the second opening segment 136 has a second diameter. The first diameter may be, for example, smaller than the second diameter.

As shown in FIGS. 11-20, the engagement member 140 has a first end 142 and a second end 144. The engagement member 140 is removably coupled to the body 110 at the first end 142. The engagement member 140 includes a base member 146 with a through hole 148 extending through the base member 146 from the first end 142 to the second end 144. The base member 146 also includes a first slot 150 extending from the second end 144 toward the first end 142 through a portion of the base member 146. The first slot 150 may, for example, bisect, intersect, or overlap with the through hole 148. The first slot 150 may also form, for example, two portions or two arms near the second end 144 of the base member 146.

The engagement member 140 may also include a first leg member or first deformable member 152 coupled to a portion of one of the two arms of the base member 146 and a second leg member or second deformable member 154 coupled to a portion of the other of the two arms of the base member 146. The first and second leg members 152, 154 may be, for example, elastically deformable or resiliently biased, such that the leg members 152, 154 may be deformed or are biased outwardly when coupled to the coupling member 130. A portion of each leg member 152, 154 may be coupled to the base member 146 at a position between the first end 142 and the second end 144. Each leg member 152, 154 may also have a first portion that extends away from the base member 146 toward the second end 144 of the engagement member 140. The portion of the leg members 152, 154 extending from the second end 144 toward the first end 142 may be, for example, tapered along a portion of the length of the engagement member 140. The tapered portion may, for example, extend from the second end 144 past the portion of each leg member 152, 154 coupled to the base member 146. An opening 156 may extend from the second end 144 into the engagement member 140 between the leg members 152, 154. The opening 156 may also extend from the second end 144 until the opening 156 engages the through hole 148. The engagement member 140 may also include a second slot 158 extending into the engagement member 140 from the second end 144 and positioned between the leg members 152, 154. The second slot 158 may, for example, bisect, intersect, or overlap the second opening 156. The second slot 158 may also be, for example, aligned with the first slot 150.

Each leg member 152, 154 may also include a second portion that extends from the portion of each leg member 152, 154 coupled to the base member 146 to the first end 142. The second portion of each leg member 152, 154 may, for example, surround and be spaced apart from the base member 146. A first aperture 160 may be positioned between the base member 146 and the first leg member 152. The first aperture 160 extends from the first end 142 to the portion of the first leg member 152 coupled to the base member 146. The first aperture 160 is positioned adjacent to a first interior surface 162 of the first leg member 152. The first interior surface 162 may include a first interior groove 164. The first interior groove 164 may be inset into the first interior surface 162 of the first leg member 152. The first interior groove 164 may extend circumferentially around the interior surface 162 of the first leg member 152. The first interior groove 164 may be, for example, sized and shaped or configured to receive at least a portion of the protrusion 132 and at least one locking tooth 134 of the coupling member 130 of the body 110. A second aperture 166 may be positioned between the base member 146 and the second leg member 154. The second aperture 166 extends from the first end 142 to the portion of the second leg member 154 coupled to the base member 146. The second aperture 166 is positioned adjacent to a second interior surface 168 of the second leg member 154. The second interior surface 168 may include a second interior groove 170. The second interior groove 170 may be inset into the second interior surface 168 of the second leg member 154. The second interior groove 170 may extend circumferentially around the interior surface 168 of the second leg member 154. The second interior groove 170 may be, for example, sized and shaped or configured to receive at least a portion of the protrusion 132 and at least one locking tooth 134 of the coupling member 130 of the body 110.

As shown in FIGS. 1-10, the insertion instrument 100 may be assembled by aligning the coupling member 130 of the body 110 with the first and second apertures 160, 166 of the engagement member 140. The coupling member 130 may then be inserted into the engagement member 140 until the protrusion 132 of the coupling member 130 engages the first interior groove 164 and the second interior groove 170.

Figure 21:
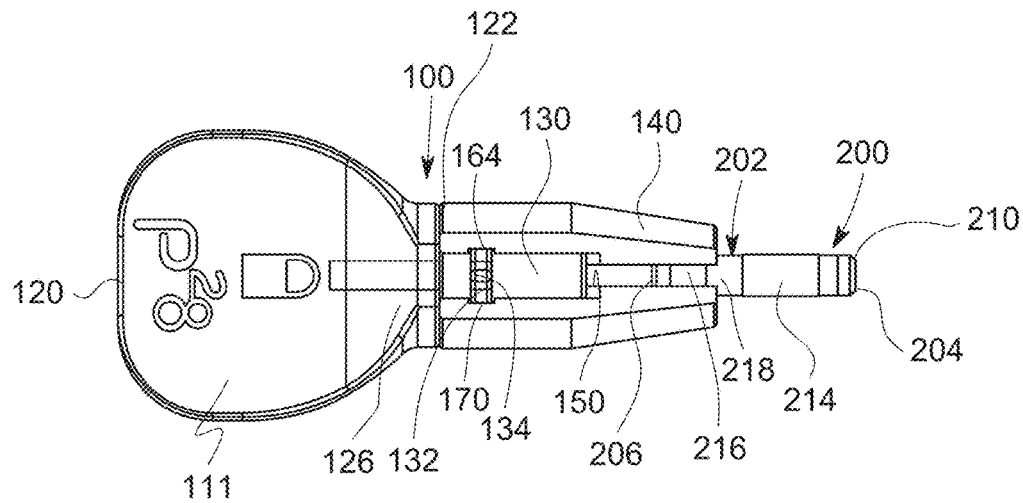
FIG. 21 is a top view of the insertion instrument of FIG. 1 with an implant positioned within the insertion instrument in an unlocked position, in accordance with an aspect of the present disclosure.
Figure 22:
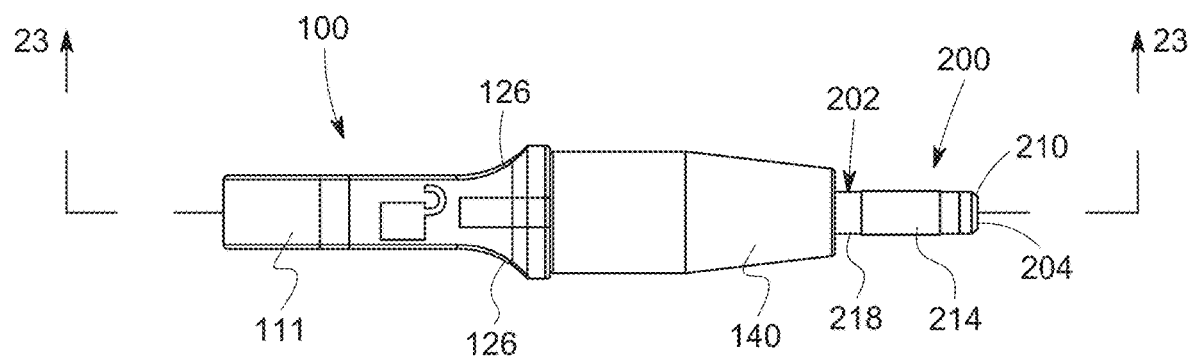
FIG. 22 is a side view of the insertion instrument and implant of FIG. 21, in accordance with an aspect of the present disclosure.
Figure 23:
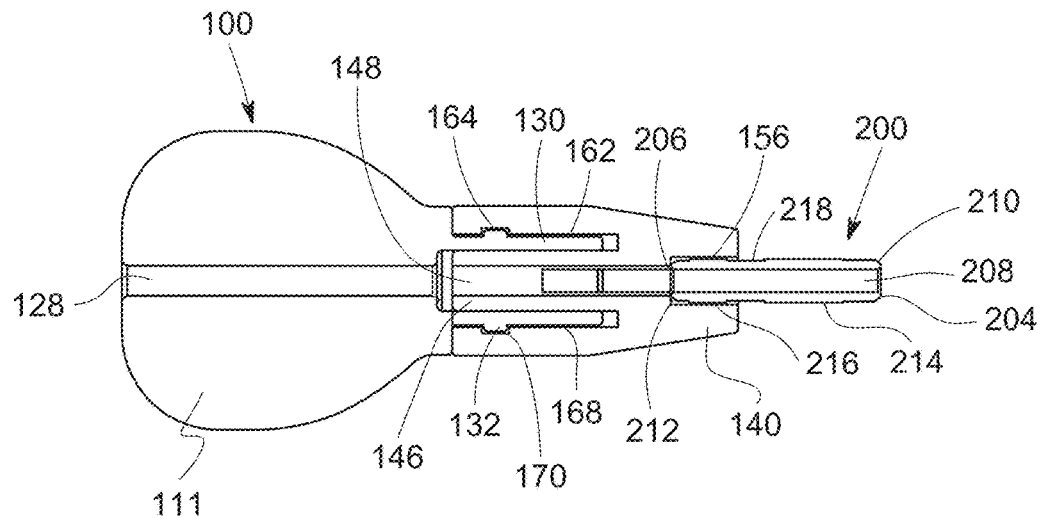
FIG. 23 is a cross-sectional top view of the insertion instrument and implant of FIG. 21 taken along line 23-23 in FIG. 22, in accordance with an aspect of the present disclosure.
Figure 24:
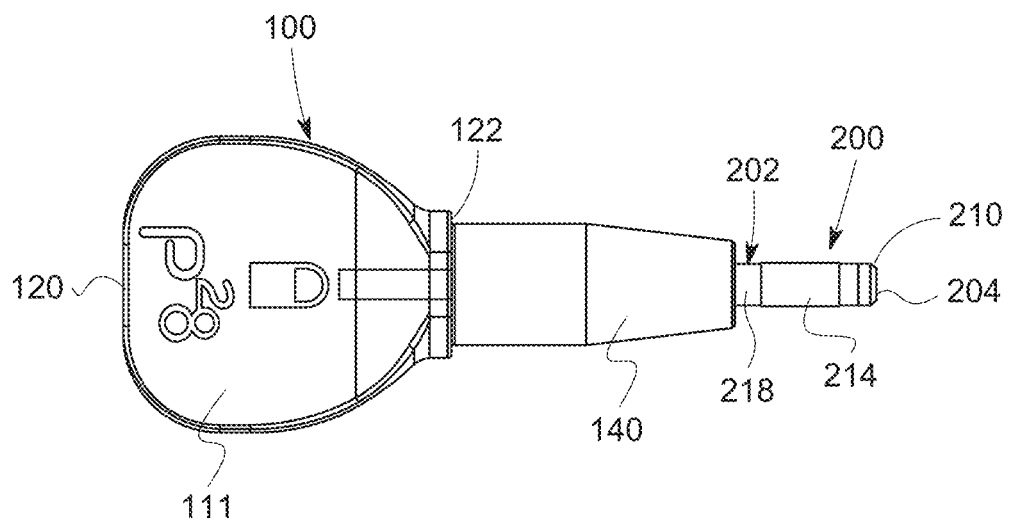
FIG. 24 is a top view of the insertion instrument and implant of FIG. 21 in a locked position, in accordance with an aspect of the present disclosure.
Figure 25:
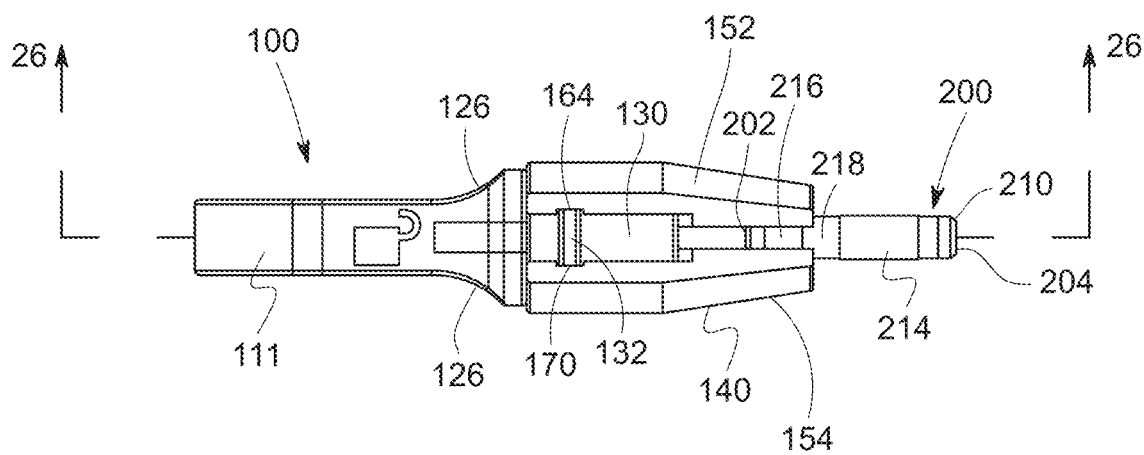
FIG. 25 is a side view of the insertion instrument and implant of FIG. 24, in accordance with an aspect of the present disclosure.
Figure 26:
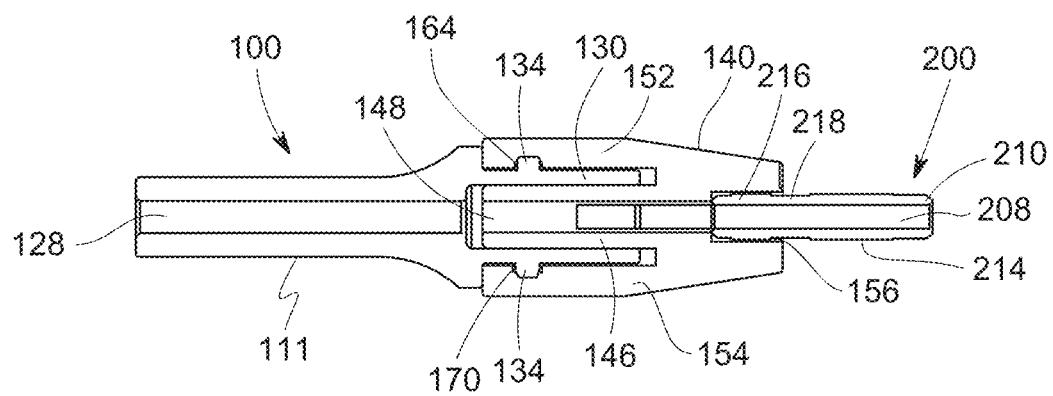
FIG. 26 is a cross-sectional top view of the insertion instrument and implant of FIG. 24 taken along line 26-26 in FIG. 25, in accordance with an aspect of the present disclosure.

As shown in FIG. 21, the engagement member 140 may be inserted with the teeth 134 of the coupling member 130 aligned with the slots 150, 158. The leg members 152, 154 may resiliently deform or deform outwardly when the protrusion 132 of the coupling member 130 is inserted into the engagement member 140, once the protrusion 132 of the coupling member 130 is received within the interior grooves 164, 170 of the leg members 152, 154, the leg members 152, 154 may be inwardly biased and exert a preloaded or natural compressive force to the exterior surface of the coupling member 130.

An insertion system may include an insertion instrument 100 and an implant 200. The implant is shown in FIGS. 21-26 and the implant 200 includes a body portion 202 with a first end 204 and a second end 206. The implant 200 also includes an opening 208 extending through the body portion 202 from the first end 204 to the second end 206. The first end 204 may also include a tapered or angled edge 210 and the second end 206 may include a tapered or angled edge 212. The implant 200 may also include a first protrusion 214 extending circumferentially away from the body portion 202 near the first end 204 of the implant 200. The implant 200 may further include a second protrusion 216 extending circumferentially away from the body portion 202 near the second end 206 of the implant 200. The first protrusion 214 may have a first length and the second protrusion 216 may have a second length. The first length may be, for example, longer than the second length. The first and second protrusions 214, 216 may be, for example, smooth or may include a textured surface. The body 202 may include a portion or central member 218 positioned between the first protrusion 214 and the second protrusion 216. As shown in FIGS. 21, 23, 25, and 26, the portion 218 of the body 202 is aligned with the first and second protrusions 214, 216 to form a straight implant 200. The implant may be, for example, as described in greater detail in U.S. application Ser. No. 15/900,528 filed Feb. 20, 2018, as well as its parent applications, and U.S. application Ser. No. 15/920,615, filed Mar. 14, 2018, as well as its parent applications, which are each incorporated herein by reference in their entireties. The parent applications of U.S. application Ser. No. 15/900,528 include International Application No. PCT/US2018/018821 filed Feb. 20, 2018, which claims priority to U.S. provisional application No. 62/461,201 filed Feb. 20, 2017, each entitled Implants, Devices, Instruments, Systems and Methods of Forming and Implanting, which are each incorporated herein by reference in their entireties. The parent application of U.S. application Ser. No. 15/920,615 include International Application No. PCT/US2018/022079 filed Mar. 12, 2018, each entitled Bone Implant Devices, Instruments and Methods of Use, which claims priority to U.S. provisional application No. 62/469,748 filed Mar. 10, 2017, and entitled Bone Implant Device, which are each incorporated herein by reference in their entireties The insertion system may be used by, for example, inserting the implant 200 into the engagement member 140 with the insertion instrument 100 in an unlocked position. The unlocked position includes the teeth 134 of the coupling member 130 aligned with the slots 150, 158 of the engagement member 140. For example, the second end 206 of the implant 200 may be inserted into the first opening 156 of the engagement member 140. A portion of the exterior surface of the implant 200 may engage the first interior surface 162 of the first leg member 152 and a portion of the exterior surface of the implant 200 may engage the second interior surface 168 of the second leg member 154. Once at least the second protrusion 216 of the implant 200 is positioned within the first opening 156 of the engagement member 140, the handle portion 111 may be, for example, rotated with respect to the engagement member 140 into a locked position. As the handle portion 111 is rotated, the coupling member 130 likewise rotates relative to the engagement member 140 and the teeth 134 of the coupling member 130 engage the interior grooves 164, 170 of the engagement member 140 to secure the implant 200 within the insertion instrument 100. After insertion of the first protrusion 214 into a patient's bone segment, the handle portion 111 may be rotated to realign the teeth 134 of the coupling member 130 with the slots 150, 158 of the engagement member 140. Once in the unlocked position, the insertion instrument 100 may be removed from the implant 200 and the surgical procedure may be completed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

As may be recognized by those of ordinary skill in the art based on the teachings herein, numerous changes and modifications may be made to the above-described and other embodiments of the present disclosure without departing from the scope of the disclosure. The components of the instruments, implants, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, implants, and/or systems may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

Having thus described the preferred embodiments, the invention is now claimed to be:

1. An implant insertion and removal system, comprising:
   an insertion instrument, comprising:
      a body portion, comprising:
         a handle portion at a first end of the body portion; and
         a coupling member extending away from the handle portion to a second end of the body portion; and
      an engagement member rotatably coupled to the coupling member, wherein the engagement member comprises:
         a base member with a first end and a second end, wherein the base member includes a first slot extending into the base member from the first end;
         a first deformable member, wherein a portion of the first deformable member is coupled to a first end of the base member; and
         a second deformable member, wherein a portion of the second deformable member is coupled to a first end of the base member on a side opposite where the portion of the first deformable member is coupled to the base member.

2. The system of claim 1, wherein the coupling member comprises:
   a base portion extending away from a second end portion of the handle portion;
   a protrusion extending circumferentially around the base portion between the second end portion of the handle portion and a second end of the base portion; and
   at least one tooth positioned on and extending away from the protrusion.

3. The system of claim 2, wherein the at least one tooth is two teeth with a first tooth positioned on the protrusion opposite a second tooth.

4. The system of claim 2, wherein the coupling member further comprises:
   a first opening segment extending into the coupling member from the second end of the body portion towards a first end along a longitudinal axis of the body portion.

5. The system of claim 1, wherein the handle portion comprises:
   a top surface;
   a bottom surface opposite the top surface, wherein the top surface and the bottom surface are planar and extend from the first end toward the second end portion; and
   a neck portion positioned at the second end portion; and wherein the neck portion includes tapered surfaces extending from the planar top and bottom surfaces to the second end portion.

6. The system of claim 5, wherein the handle portion further comprises:
   a second opening segment extending into the handle portion from a first end portion to the second end portion along a longitudinal axis.

7. The system of claim 1, wherein the first deformable member and the second deformable member each include a first portion extending away from the coupled portion toward the first end of the engagement member, and wherein the first portion extends beyond a first end of the base member.

8. The system of claim 7, wherein the first deformable member and the second deformable member each include a second portion extending away from the coupled portion toward a first end of the engagement member, and wherein the second portion extends to a position parallel with the first end of the base member.

9. The system of claim 8, wherein the first deformable member is spaced apart from the base member by a first aperture, and wherein the second deformable member is spaced apart from the base member by a second aperture; and wherein the first aperture forms a first interior surface on the first deformable member, and wherein the second aperture forms a second interior surface on the second deformable member.

10. The system of claim 9, wherein the first deformable member includes a first groove inset into the first interior surface perpendicular to the longitudinal axis of the engagement member, and wherein the second deformable member includes a second groove inset into the second interior surface perpendicular to the longitudinal axis of the engagement member.

11. The system of claim 10, wherein a portion of the coupling member is positioned within the first aperture and the second aperture; and wherein an exterior surface of the coupling member engages the first interior surface and the second interior surface of the engagement member.

12. The system of claim 10, wherein at least a portion of a protrusion of the coupling member is positioned within the first groove and the second groove.

13. The system of claim 1, further comprising:
   an implant, wherein the implant comprises:
      a body portion with a first end and a second end;
      a first protrusion extending circumferentially away from the body portion, the first protrusion positioned between the first end and a central member of the body portion; and
      a second protrusion extending circumferentially away from the body portion, the second protrusion positioned between the central member and the second end of the body portion.

14. The system of claim 13, wherein the implant further comprises:
   an opening extending through the body from the first end to the second end.

15. The system of claim 14, wherein a first body portion is formed between the first end and the central member, and wherein a second body portion is formed between the central member and the second end.

16. The system of claim 15, wherein the first body portion is aligned along a longitudinal axis with the second body portion.

17. The system of claim 16, wherein the first body portion is angled relative to the second body portion.

18. The system of claim 1, wherein at least a portion of the implant is received within a portion of the first slot of the engagement member.

19. A surgical method, comprising:
   exposing a patient's joint;
   inserting a first k-wire into a base of a middle phalanx proximally;
   retrograding the first k-wire from a tip of a toe, across a distal phalanx and the middle phalanx;
   inserting the first k-wire into a proximal phalanx;
   pulling the first k-wire to position a tip of the first k-wire in the joint;
   inserting a second k-wire into the proximal phalanx;
   driving a drill across the second k-wire and into the proximal phalanx;
   removing the second k-wire from the patient's joint;

driving the drill and the first k-wire into the middle phalanx;

inserting an implant into the proximal phalanx and the middle phalanx using the insertion instrument of claim 1.

* * * * *